United States Patent [19]

Gibbs

[11] 4,321,200
[45] Mar. 23, 1982

[54] ARYLTHIOUREIDOISOINDOLINES
[75] Inventor: Charles G. Gibbs, Shawnee Mission, Kans.
[73] Assignee: Gulf Oil Corporation, Pittsburgh, Pa.
[21] Appl. No.: 224,369
[22] Filed: Jan. 12, 1981

Related U.S. Application Data
[62] Division of Ser. No. 124,992, Mar. 13, 1980, Pat. No. 4,272,284.

[51] Int. Cl.$^3$ .......................................... C07D 209/44
[52] U.S. Cl. .................................. 260/326.1; 71/96; 71/76
[58] Field of Search ............................... 260/326.1

[56] References Cited
U.S. PATENT DOCUMENTS
4,264,502  4/1981  Patel et al. ................... 260/326.5

OTHER PUBLICATIONS
Chem. Substance Index, Chem. Abstract, 91, 5693CS.

*Primary Examiner*—Henry R. Jiles
*Assistant Examiner*—Jane T. Fan
*Attorney, Agent, or Firm*—Deane E. Keith; Forrest D. Stine; Carl A. Cline

[57] ABSTRACT

A novel class of compounds which are useful as plant growth regulators has the general structural formula

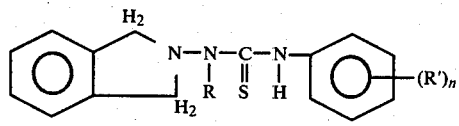

in which R is H or $CH_3$, R' is halogen, trifluoromethyl, cyano or $C_1$ to $C_3$ alkyl or alkoxy and n is zero or an integer from 1 to 2.

The compounds are synthesized by reacting a compound of the formula

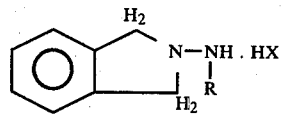

with an isocyanate of the formula

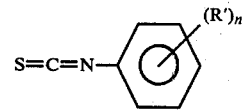

under basic conditions in a non-reactive, polar organic solvent.

23 Claims, No Drawings

ARYLTHIOUREIDOISOINDOLINES

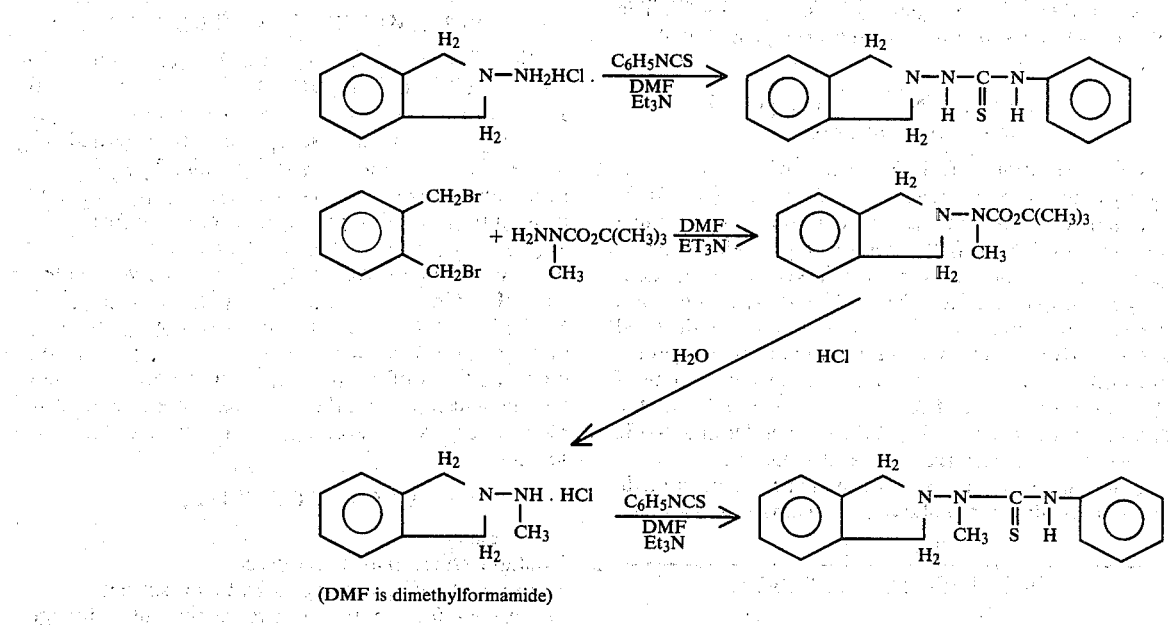

(DMF is dimethylformamide)

This is a division of application Ser. No. 124,992 filed Mar. 13, 1980, now U.S. Pat. No. 4,272,284, issued June 9, 1981.

DESCRIPTION OF THE INVENTION

I have discovered a novel class of compounds which are useful as growth regulators, particularly for the purpose of yield enhancement or increasing the fruit set of crop plants. The novel compounds have the general structural formula

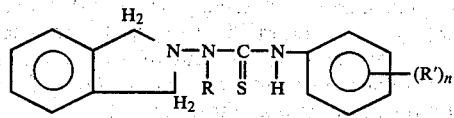

in which R is H or $CH_3$, R' is halogen, trifluoromethyl, cyano or $C_1$ to $C_3$ alkyl or alkoxy and n is zero or an integer from 1 to 2. This invention is also directed to a method of synthesis of the novel class of compounds and use of the compounds to regulate growth of plants.

SYNTHESIS OF THE GROWTH REGULATORS

The novel growth regulator compounds of this invention may be made by means of the general reaction outlined below;

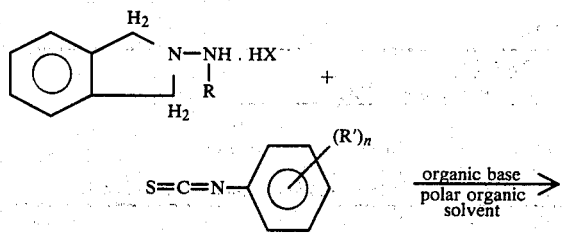

in which HX represents hydrochloric or other strong acid. The organic base, which serves as an acid acceptor, is preferably a strongly basic organic amino compound, such as triethylamine. Specific procedures are outlined and exemplified below for illustrative purposes:

The N-amino dihydroisoindole hydrochloride is prepared as taught by L. A. Carpino, J.A.C.S., 79, 4427(1957). The t-butyl 2-methyl-carbazate is prepared as taught by A. S. Dutta and J. S. Morley, J.C.S. Perkin I, 1712(1975). Below are specific, illustrative procedures.

Preparation of N-(phenylthioureido)-dihydroisoindole

To a solution of 1.7 g (0.01 mole) of N-amino dihydroisoindole hydrochloride in 10 ml of dimethyl formamide was added 1 ml of triethylamine followed by 1.35 g (0.01 mole) of phenylisothiocyanate. The reaction mixture was allowed to stir at room temperature overnight. Water (25 ml) was added, the mixture stirred for 1 hr., and filtered. After drying there was obtained 2.6 g of the desired product, mp: 192°–193° dec. The IR and NMR were consistent with the proposed structure.

Preparation of N-(t-butyloxy carbonyl-methylamino)dihydroisoindole

A vigorously stirred solution 13.15 g (0.05 mole) of o-xylylene dibromide and 7.3 g (0.05 mole) of t-butyl 2-methylcarbazate in 25 ml of dimethylformamide was warmed to 50° and 14 ml of triethylamine was added during 5–8 minutes while maintaining the temperature at 50°–60°. After complete addition the reaction mixture was stirred at room temperature for 3 hrs. and diluted with 100 ml of water. After stirring for 1 hr the mixture was extracted with ethyl acetate. The organic phase was separated and dried. Filtration and evaporation gave a gummy solid which was used without further purification. The IR and NMR of the material were consistent with the proposed structure.

Preparation of N-methylaminodihydroisoindole hydrochloride

To the crude N-(t-butyloxycarbonyl-N-methylamino)dihydroisoindole from the above preparation was added 25 ml of concentrated hydrochloric acid. The reaction mixture was allowed to stir for one hour. Evaporation of the mixture to dryness and recrystallization of the residue from ethanolether gave 5.6 g of the desired product as a gummy solid, mp: 79°–89°. The IR and NMR were consistent with the proposed structure.

Preparation of N-(1-methyl-3-phenyl thioureido)dihydroisoindole

To a solution of 1.12 g (0.006 mole) of N-methylamino dihydroisoindole hydrochloride in 10 ml of dimethylformamide was added 1 ml of triethylamine followed by 0.82 g (0.006 mole) of phenylisothiocyanate. The reaction mixture was allowed to stir at room temperature overnight. Water (25 ml) was added and the resulting gummy solid was extracted with ethyl acetate. After drying and filtering, evaporation gave a thick oil which solidified upon adding a small amount of ether and scratching. There was obtained 1.4 g of the desired product, mp: 121°–125° dec. The IR and NMR were consistent with the proposed structure.

Compounds of the invention which have been made by methods illustrated above are disclosed in Table I.

TABLE I

COMPOUNDS OF THE FORMULA

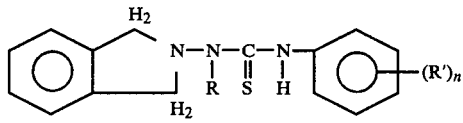

| M-No | m.p. °C. | R | (R')$_n$ |
|------|----------|------|----------|
| 3987 | 192-3°   | H    | H        |
| 4053 | 183-4    | H    | 3-CH$_3$ |
| 4054 | 177-9    | H    | 3-Cl     |
| 4055 | 184-6    | H    | 4-F      |
| 4056 | 176-9    | H    | 2-F      |
| 4057 | 177-180  | H    | 4-CF$_3$ |
| 4249 | 121-5    | CH$_3$ | H      |
| 4250 | 134-142  | CH$_3$ | 4-Cl   |
| 4251 | 104-113  | CH$_3$ | 3-Cl   |
| 4252 | 149-156  | CH$_3$ | 4-F    |
| 4253 | 128-138  | CH$_3$ | 3-F    |
| 4322 | 208-210  | H    | 3-CN     |
| 4323 | 174-177  | H    | 3-F      |
| 4324 | 87-102   | H    | 4-Cl     |
| 4325 | 185-188  | H    | 4-CH$_3$ |
| 4326 | 171-176  | H    | 2,4-Cl$_2$ |
| 4327 | 166-172  | H    | 3,4-Cl$_2$ |
| 4424 | 192-193  | H    | 2-Cl     |
| 4425 | 171-174  | H    | 2,3-Cl$_2$ |
| 4426 | 183-187  | H    | 4-OCH$_3$ |
| 4427 | 198-199  | H    | 2-CH$_3$ |
| 4428 | 174-177  | H    | 3,4-(CH$_3$)$_2$ |

USE OF THE GROWTH REGULATORS

The effects of these compounds as growth regulators, resulting from both pre-emergent and post-emergent application are often readily apparent. These effects may be demonstrated by means of the following illustrative procedures.

PRE-EMERGENT APPLICATION

Disposable paper trays about 2½ inches deep were filled with soil and sprayed with aqueous spray mixtures at a rate of 5 lb. of active chemical per acre of sprayed area, were seeded with 6 species of plant seeds and were then covered with about ¼ inch of soil. The spray mixtures were prepared by dissolving the proper amount of growth regulator compound in 15 ml of acetone, adding 4 ml of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 60 ml by addition of warm water. Twenty-one days after seeding and treatment the plantings were examined and plant injury was rated according to the following schedule:

DEGREE OF EFFECT

0 = no effect
1 = slight effect, plants recovered
2 = moderate effect, injury to 26 to 75 percent
3 = severe effect, injury to 76 to 93 percent of foliage
4 = maximum effect (all plants died)

POST-EMERGENT APPLICATION

Several species of plants were grown in potting soil in disposable styrofoam trays and tomatoes were grown in four-inch pots in the greenhouse. Aqueous spray formulations were prepared and the growing plants were sprayed at a spray volume of 60 gallons per acre and an application rate of 5 lb. per acre. Spray mixtures were prepared in the manner described above. For comparative purposes, plants were also sprayed at 60 gal./acre with a spray mixture containing no growth regulator. Plant injury was again rated according to the schedule disclosed above and observations of growth regulator effects were observed and recorded as follows, for both pre- and post-emergent applications:

| Effect | Abbreviation in Tables |
|--------|------------------------|
| Formative effect on new growth | F |
| Epinasty | E |
| Growth reduction | G |
| Non-emergence | K |
| Necrosis | N |

In Table II below there are tabulated the observations of pre- and post-emergent herbicidal and growth regulator effects of various compounds disclosed above.

TABLE II

EFFECT ON VEGETATION

| | Pre-emergent Effects | | | | | | Post-emergent Effects | | | | | |
|---|---|---|---|---|---|---|---|---|---|---|---|---|
| Compound No. | Digitaria sanguinalis | Celosia plumosa | Bromus inermis | Setaria italica | Raphanus sativus | Beta vulgaris | Setaria italica | Medicago sativa | Avena sativa | Raphanus sativus | Beta vulgaris | Lycopersicum esculentum | Comments |
| 3987 | 0 | 0 | F1 | 0 | 0 | 0 | 0 | F2G1 | 0 | 0 | F2G2 | F2 | |
| 4053 | 0 | F1 | F1 | F1 | 0 | F2G1 | F1 | F3G1 | F1 | F1 | F3G1 | F1 | Increased fruit set |
| 4055 | 0 | 0 | F2G1 | 0 | 0 | F1 | F1 | F3G3 | F1 | F1 | F3G3 | F1 | Increased tillering |
| 4056 | 0 | F1 | F2 | 0 | 0 | F2G1 | F1 | F3G3 | F1 | 0 | F3G3 | F1 | Increased tillering |
| 4057 | 0 | F1 | F1 | 0 | 0 | F1 | 0 | F3G1 | 0 | F1 | F2 | 0 | |
| 4249 | 0 | 0 | 0 | 0 | 0 | 0 | F1 | F2G1 | — | F1 | F1G1 | F1 | |

TABLE II-continued

EFFECT ON VEGETATION

| | Pre-emergent Effects | | | | | | Post-emergent Effects | | | | | |
|---|---|---|---|---|---|---|---|---|---|---|---|---|
| Compound No. | Digitaria sanguinalis | Celosia plumosa | Bromus inermis | Setaria italica | Raphanus sativus | Beta vulgaris | Setaria italica | Medicago sativa | Avena sativa | Raphanus sativus | Beta vulgaris | Lycopersicum esculentum | Comments |
| 4250 | 0 | 0 | 0 | 0 | 0 | 0 | F1 | F2G1 | — | F1 | F1G1 | F1 | |
| 4251 | 0 | 0 | 0 | 0 | 0 | 0 | F2G1 | F1 | F1 | F1 | F3G1 | F2 | Increased fruit set |
| 4252 | 0 | 0 | 0 | 0 | 0 | 0 | 0 | 0 | 0 | 0 | F1 | 0 | |
| 4253 | 0 | 0 | 0 | 0 | 0 | 0 | F1 | F2 | F1 | F2G1 | F2G1 | F2 | Increased fruit set |
| 4322 | 0 | 0 | 0 | 0 | 0 | 0 | N1 | F1 | 0 | 0 | F1 | F1 | |
| 4323 | F2G1 | F2G2 | F2G1 | 0 | F1G1 | F1 | F3G2 | F1 | F1 | F3G1 | F2 | | |
| 4324 | 0 | 0 | 0 | 0 | 0 | 0 | 0 | F2G1 | 0 | F1 | F2 | F1 | |
| 4325 | 0 | 0 | F1G1 | F1G1 | 0 | F1 | 0 | F2G1 | F1 | 0 | F2 | F1 | |
| 4326 | 0 | 0 | 0 | 0 | 0 | F1 | F1 | F2G1 | F1 | F1 | F2 | F2 | |
| 4327 | F3G2 | F2G1 | F3G1 | F3G3 | 0 | F1 | 0 | F3G1 | 0 | 0 | F1 | F1 | Increased fruit set |
| 4424 | 0 | 0 | 0 | 0 | 0 | 0 | N1 | F1 | 0 | 0 | F1 | 0 | |
| 4426 | 0 | 0 | 0 | 0 | 0 | 0 | 0 | F1 | 0 | 0 | F1 | F1 | |
| 4427 | 0 | 0 | 0 | 0 | 0 | 0 | 0 | 0 | 0 | 0 | F1 | F1 | |
| 4428 | 0 | 0 | 0 | 0 | 0 | 0 | 0 | F1 | 0 | 0 | F1 | F1 | |

The use of many of the growth regulator compounds may be demonstrated by treatment of soybeans (*Soja max*) to increase the number of seed pods and by treating tomato plants (*Lycopersicum esculentum*) to increase fruit set. In an illustrative experiment, *Soja max* (Evans variety) and *Lycopersicum esculentum* (Tiny Tim variety) were grown in 4-inch pots (one plant per pot) filled with greenhouse potting soil (2 parts good top soil, 1½ parts builders' sand, 1½ parts peat, fertilized with 5 lb. of 12-12-6 fertilizer and 5 lb. of finely ground limestone per cu. yd.). Aqueous spray formulations were prepared and the potted plants were sprayed at a spray volume of 40 gal. per acre and at application rates of 16, 4, 1 and ¼ oz. per acre. The spray mixtures were prepared by dissolving the proper amount of growth regulator compound in 15 ml. of acetone, adding 2 ml. of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 80 ml by addition of a 0.156 wt. percent aqueous solution of liquid non-ionic dispersant (90 wt. percent active trimethylnonyl polyethylene glycol ether, Tergitol TMN-10). Two replicates were sprayed at all application rates. For comparative purposes, plants were also sprayed at 40 gal./acre with water. The number of seed pods and of fruits on both treated and on untreated plants was observed within approximately three weeks after spray treatment and the results are tabulated below as averages of two replicates. The fruit set is expressed as percentage of average pod or fruit count on treated plants, in comparison with average count on untreated plants. The severity of growth regulatory effect on the plants was estimated on a scale of 0 to 10 and is also recorded in the following table:

TABLE III

GROWTH REGULATING EFFECTS ON TWO SPECIES

| | | Lycopersicum esculentum | | Soja max | |
|---|---|---|---|---|---|
| | | | Fruit Count Percent in | | Pod Count Percent in |
| Comp'd. No. | Rate oz/A | Severity of Growth Regulating Effect | Comparison to Untreated Plants | Severity of Growth Regulating Effect | comparison to Untreated Plants |
| 3987 | 16 | 0 | 100 | 3.5 | 123 |
| | 4 | 0 | 50 | 0.5 | 98 |
| 4053 | 16 | 1.5 | 400 | 1.5 | 101 |
| | 4 | 0 | 200 | 1 | 91 |
| | 1 | 0 | 300 | 0 | 101 |
| 4054 | 16 | 0 | 200 | 0.5 | 105 |
| | 4 | 0 | 600 | 0 | 105 |
| | 1 | 0 | 100 | 0 | 94 |
| 4055 | 16 | 0.5 | 300 | 1.5 | 153 |
| | 4 | 0 | 100 | 0 | 115 |
| | 1 | 0 | 0 | 0 | 87 |
| 4056 | 16 | 0.5 | 400 | 2.5 | 112 |
| | 4 | 0.5 | 300 | 0.5 | 129 |
| | 1 | 0 | 100 | 0 | 80 |
| 4057 | 16 | 0 | 100 | 1.5 | 167 |
| | 4 | 0 | 200 | 1 | 122 |
| | 1 | 0 | 100 | 0 | 129 |
| 4249 | 16 | 0 | 150 | 3.5 | 93 |
| | 4 | 0 | 175 | 0.5 | 105 |
| | 1 | 0 | 150 | 0 | 89 |
| 4250 | 16 | 0 | 113 | 0 | 93 |
| | 4 | 0 | 125 | 0 | 105 |
| | 1 | 0 | 113 | 0 | 114 |
| 4251 | 16 | 1 | 175 | 0.5 | 73 |
| | 4 | 0 | 113 | 0 | 93 |
| | 1 | 0 | 100 | 0 | 93 |
| 4252 | 16 | 0 | 113 | 1.5 | 89 |
| | 4 | 0 | 113 | 0 | 109 |
| | 1 | 0 | 100 | 0 | 81 |
| 4253 | 16 | 1.5 | 113 | 1 | 97 |
| | 4 | 0.5 | 88 | 0 | 89 |
| | 1 | 0 | 113 | 0 | 93 |
| 4310 | 16 | 0 | 87 | 0 | 96 |
| | 4 | 0 | 106 | 0 | 118 |
| | 1 | 0 | 144 | 0 | 96 |
| 4322 | 16 | 0 | 136 | 0 | 114 |
| | 4 | 0 | 150 | 0 | 91 |
| | 1 | 0 | 95 | 0 | 105 |
| 4326 | 16 | 0.5 | 177 | 1 | 118 |
| | 4 | 0 | 150 | 0 | 118 |
| | 1 | 0 | 150 | 0 | 105 |

The information presented in tabular form herein will enable a worker in the art to make a selection from among the growth regulator compounds of the invention and to make some judgment with regard to application rates, depending upon the effect which is desired. It may be seen, for example, that severe effects on some species of vegetation may occur at application rates of only 5 lb. per acre, whereas beneficial effects may be observed on living plants at application rates of 1 lb. per acre or less.

The growth regulator compounds are usually applied in combination with inert carriers or diluents, as in aqueous sprays, granules and dust formulations in accordance with established practice in the art. An aqueous spray is usually prepared by mixing a wettable powder or emulsifiable formulation of a growth regulator with a relatively large amount of water to form a dispersion.

Wettable powders comprise intimate, finely divided mixtures of growth regulator compounds, inert solid carriers and surface active agents. The inert solid carrier is usually chosen from among the attapulgite clays, the kaolin clays, the montmorillonite clays, the diatomaceous earth, finely divided silica and purified silicates. Effective surfactants, which have wetting, penetrating and dispersing ability are usually present in a wettable powder formulation in proportions of from 0.5 to about 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates of the growth regulator compounds comprise in each instance, a solution of growth regulator compound in a liquid carrier which is a mixture of water-immiscible solvent and surfactants, including emulsifiers. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

Usually, the growth regulators are applied by diluting with water agricultural compositions which desirably contain from 0.1 percent to 95 percent by weight of active compound and from 0.1 to 75 percent of a carrier or surfactant. However, direct application to plant seeds prior to planting may be accomplished in some instances by mixing powdered solid growth regulator with seed to obtain a substantially uniform coating which is very thin and comprises only one or two percent by weight or less, based on the weight of the seed. In most instances, however, a nonphytotoxic solvent, such as methanol is employed as a carrier to facilitate the uniform distribution of growth regulator on the surface of the seed.

When a compound is to be applied to the soil, as for a pre-emergence application, granular formulations are sometimes more convenient than sprays. A typical granular formation comprises the growth regulator compound dispersed on an inert carrier such as coarsely ground clay, or clay which has been converted to granules by treatment of a rolling bed of the powdered material with a small amount of liquid in a granulating drum.

In the usual process for preparing granular formulations, a solution of the active compound is sprayed on the granules while they are being agitated in a suitable mixing apparatus, after which the granules are dried with a current of air during continued agitation.

I claim:

1. A compound having the structural formula

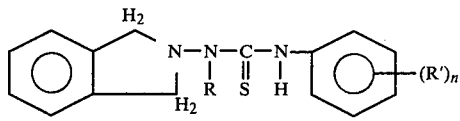

in which R is H or $CH_3$, R' is halogen, trifluoromethyl, cyano or $C_1$ to $C_3$ alkyl or alkoxy and n is zero or an integer from 1 to 2.

2. A compound of claim 1 in which R is H and n is zero.

3. A compound of claim 1 in which R is H and $(R')_n$ is 3-methyl.

4. A compound of claim 1 in which R is H and $(R')_n$ is 3-chloro.

5. A compound of claim 1 in which R is H and $(R')_n$ is 4-fluoro.

6. A compound of claim 1 in which R is H and $(R')_n$ is 2-fluoro.

7. A compound of claim 1 in which R is H and $(R')_n$ is 4-trifluoromethyl.

8. A compound of claim 1 in which R is $CH_3$ and n is zero.

9. A compound of claim 1 in which R is $CH_3$ and $(R')_n$ is 4-chloro.

10. A compound of claim 1 in which R is $CH_3$ and $(R')_n$ is 3-chloro.

11. A compound of claim 1 in which R is $CH_3$ and $(R')_n$ is 4-fluoro.

12. A compound of claim 1 in which R is $CH_3$ and $(R')_n$ is 3-fluoro.

13. A compound of claim 1 in which R is H and $(R')_n$ is 3-cyano.

14. A compound of claim 1 in which R is H and $(R')_n$ is 3-fluoro.

15. A compound of claim 1 in which R is H and $(R')_n$ is 4-chloro.

16. A compound of claim 1 in which R is H and $(R')_n$ is 4-methyl.

17. A compound of claim 1 in which R is H and $(R')_n$ is 2,4-dichloro.

18. A compound of claim 1 in which R is H and $(R')_n$ is 3,4-dichloro.

19. A compound of claim 1 in which R is H and $(R')_n$ is 2-chloro.

20. A compound of claim 1 in which R is H and $(R')_n$ is 2,3-dichloro.

21. A compound of claim 1 in which R is H and $(R')_n$ is 4-methoxy.

22. A compound of claim 1 in which R is H and $(R')_n$ is 2-methyl.

23. A compound of claim 1 in which R is H and $(R')_n$ is 3,4-dimethyl.

* * * * *

UNITED STATES PATENT OFFICE
CERTIFICATE OF CORRECTION

Patent No. 4,321,200  Dated  March 23, 1982

Inventor(s)  Charles G. Gibbs

It is certified that error appears in the above-identified patent and that said Letters Patent are hereby corrected as shown below:

Table II, Compound No. 4250, under "Post-emergent Effects", subheadings "Medicago sativa F2G1, Avena sativa —, Raphanus sativus F1, Beta vulgaris F1G1, Lycopersicum esculentum F1" should read --Medicago sativa F1, Avena sativa 0, Raphanus sativas 0, Beta vulgaris F1, Lycopersicum esculentum 0--.

Table II, Compound No. 4323 under "Pre-emergent Effects", subheadings "Setaria italica 0, Raphanus sativus F1G1, Beta vulgaris F1" should read --Setaria italica F2G1, Raphanus sativus 0, Beta vulgaris F1G1--.

Table II, Compound No. 4323, under "Post-emergent Effects", subheadings "Setaria italica F3G2, Medicago sativa F1, Raphanus sativus F3G1, Beta vulgaris F2, Lycopersicum esculentum" should read--Setaria italica F1, Medicago sativa F3G2, Raphanus sativus F1, Beta vulgaris F3G1, Lycopersicum esculentum F2--.

Signed and Sealed this

Seventh Day of December 1982

[SEAL]

Attest:

GERALD J. MOSSINGHOFF

Attesting Officer    Commissioner of Patents and Trademarks